US011031134B2

(12) United States Patent
Bender et al.

(10) Patent No.: US 11,031,134 B2
(45) Date of Patent: Jun. 8, 2021

(54) MONITORING INDIVIDUALS FOR WATER RETENTION MANAGEMENT

(71) Applicant: International Business Machines Corporation, Armonk, NY (US)

(72) Inventors: Michael Bender, Rye Brook, NY (US); Rhonda L. Childress, Austin, TX (US); Kim Alice Eckert, Austin, TX (US); Minh Q. Pham, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 335 days.

(21) Appl. No.: 15/888,274

(22) Filed: Feb. 5, 2018

(65) Prior Publication Data

US 2019/0244709 A1 Aug. 8, 2019

(51) Int. Cl.
*G16H 50/20* (2018.01)
*G06Q 10/10* (2012.01)
*G06N 20/00* (2019.01)
*G16H 40/67* (2018.01)
*G16H 20/10* (2018.01)
*G16H 50/30* (2018.01)

(52) U.S. Cl.
CPC ............ *G16H 50/20* (2018.01); *G06N 20/00* (2019.01); *G06Q 10/1093* (2013.01); *G16H 20/10* (2018.01); *G16H 40/67* (2018.01); *G16H 50/30* (2018.01)

(58) Field of Classification Search
CPC .......................... G16H 50/20; G06Q 50/22–24
See application file for complete search history.

(56) References Cited

U.S. PATENT DOCUMENTS

| 5,412,560 A * | 5/1995 | Dennison ............ G06F 19/3475 600/300 |
| 5,876,353 A | 3/1999 | Riff |
| 8,221,323 B2 | 7/2012 | Zhang et al. |
| 8,784,323 B2 | 7/2014 | Nabutovsky et al. |
| 2006/0030894 A1* | 2/2006 | Tehrani ................ A61N 1/3601 607/42 |
| 2007/0067181 A1* | 3/2007 | Dettinger ............... G16H 50/20 705/2 |

(Continued)

FOREIGN PATENT DOCUMENTS

| CN | 103793610 A | 5/2014 |
| WO | 2015103442 A1 | 7/2015 |

(Continued)

OTHER PUBLICATIONS

"Recommendations for how to reduce water retention"; Top Doctors; Aug. 24, 2017 (Year: 2017).*

*Primary Examiner* — John A Pauls
(74) *Attorney, Agent, or Firm* — Will Stock; Edell, Shapiro & Finnan, LLC

(57) ABSTRACT

Methods, systems, and computer program products are provided for monitoring an entity for personal water retention management. Health data for the entity is monitored via one or more sensors. Changes in the monitored health data are tracked over time. Based on the monitored health data, occurrence of a water retention triggering event associated with a provided medical recommendation is determined. When the water retention triggering event is determined to have occurred, the medical recommendation is provided to the entity.

17 Claims, 5 Drawing Sheets

(56) References Cited

U.S. PATENT DOCUMENTS

| | | | |
|---|---|---|---|
| 2010/0204593 A1* | 8/2010 | Park | A61B 5/0537 |
| | | | 600/508 |
| 2014/0155763 A1* | 6/2014 | Bruce | A61B 5/02055 |
| | | | 600/484 |
| 2014/0200487 A1 | 7/2014 | Ramdas et al. | |
| 2015/0100345 A1 | 4/2015 | Holmes et al. | |
| 2015/0120317 A1 | 4/2015 | Mayou et al. | |
| 2015/0182843 A1 | 7/2015 | Esposito et al. | |
| 2015/0216413 A1 | 8/2015 | Soyao et al. | |
| 2016/0063215 A1* | 3/2016 | Zamer | G06F 19/3481 |
| | | | 705/3 |
| 2017/0124528 A1* | 5/2017 | Chakra | G16H 10/60 |
| 2017/0277841 A1* | 9/2017 | Shankar | G06F 19/326 |
| 2018/0005194 A1* | 1/2018 | Dotan-Cohen | G06F 16/29 |
| 2018/0240238 A1* | 8/2018 | Husheer | G06T 7/62 |

FOREIGN PATENT DOCUMENTS

| | | | | |
|---|---|---|---|---|
| WO | 2016207823 A1 | 12/2016 | | |
| WO | WO-2019209753 A1 * | 10/2019 | | C12Q 1/68 |

* cited by examiner

MONITORING INDIVIDUALS FOR WATER RETENTION MANAGEMENT

BACKGROUND

1. Technical Field

Present invention embodiments relate to methods, systems and computer program products for monitoring individuals for managing systemic edema. In particular, the present invention embodiments relate to systems, methods and computer program products for receiving data from sensors, monitoring upcoming events and providing recommendations for managing systemic water retention based on the collected data or the upcoming events.

2. Discussion of the Related Art

As people grow older, water retention can become a problem. Water retention can lead to a number of health problems such as, for example, heart attacks, high blood pressure, swollen joints and a general malaise. Recognizing an onset of water retention or situations in which water retention is likely to occur would provide an individual with an opportunity to take actions in order to reduce an impact of the water retention.

SUMMARY

In a first aspect of the invention, a computer-implemented method is provided for monitoring an entity for personalized water retention management. At least one computing device monitors health data for an entity via one or more sensors. The at least one computing device tracks changes in the monitored health data over time. The at least one computing device determines, based on the monitored health data, occurrence of a water retention triggering event associated with a provided medical recommendation. The at least one computing device provides the medical recommendation to the entity when the water retention triggering event is determined to have occurred.

In a second aspect of the invention, a system is provided for personalized water retention management. The system includes at least one processor and at least one memory connected with each of the at least one processor. The at least one processor is configured to perform: monitoring health data related to systemic water retention for an entity via one or more sensors; tracking changes over time in the monitored health data; determining, based on the monitored health data, occurrence of a water retention triggering event associated with a provided medical recommendation; and providing the medical recommendation to the entity when the water retention triggering event is determined to have occurred.

In a third aspect of the invention, a computer program product is provided. The computer program product includes at least one computer readable medium having computer readable program code embodied therewith for execution on at least one processor such that the at least one processor is configured to perform: monitoring health data for an entity via one or more sensors; tracking changes over time in the monitored health data; determining, based on the monitored health data, occurrence of a water retention triggering event associated with a provided medical recommendation; and providing the medical recommendation to the entity when the water retention triggering event is determined to have occurred.

BRIEF DESCRIPTION OF THE DRAWINGS

Generally, like reference numerals in the various figures are utilized to designate like components.

DETAILED DESCRIPTION

Figure 1:
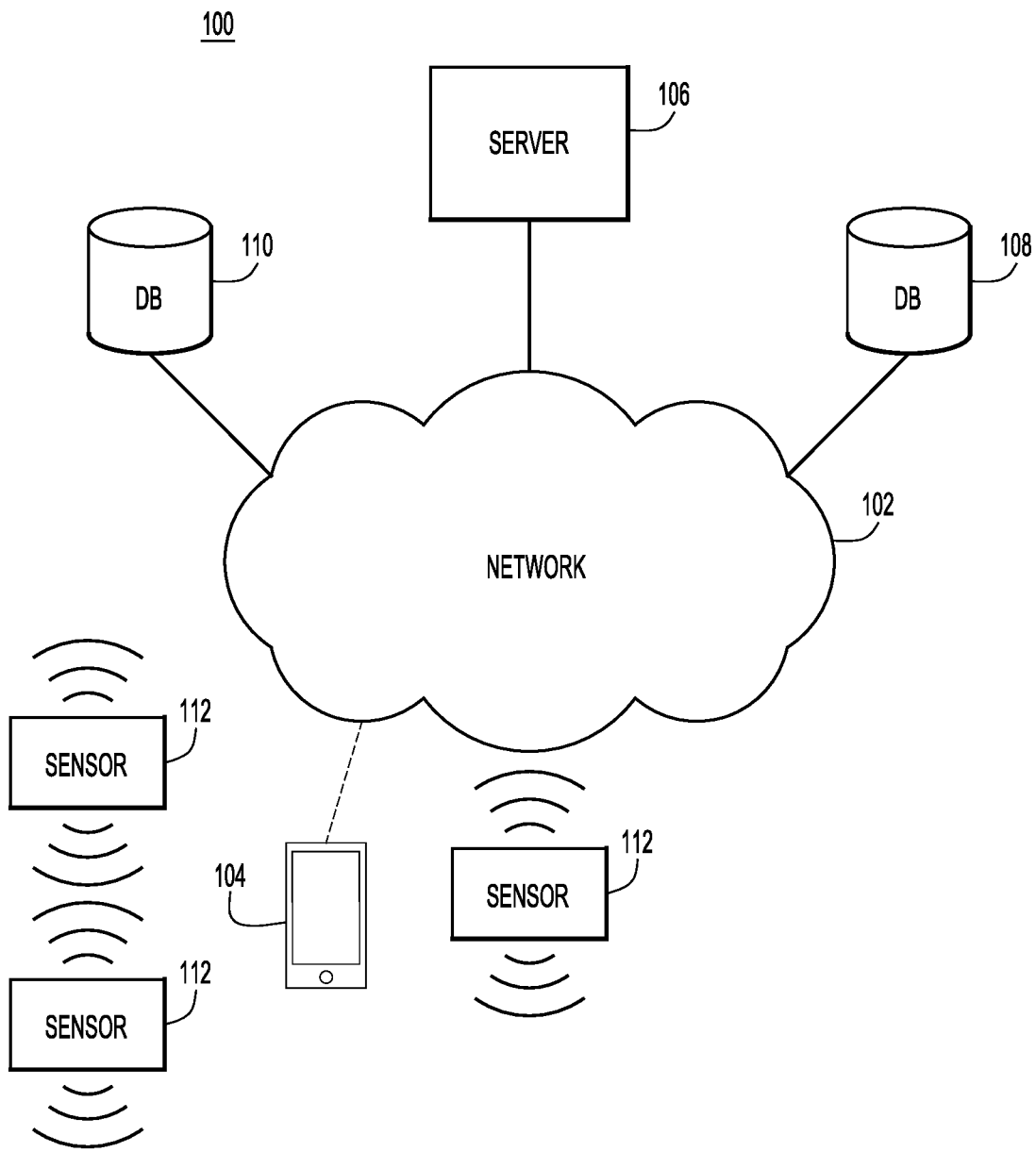
FIG. 1 illustrates an example environment in which embodiments of the invention may operate.

Various sensors, which may include Internet of Things (IoT) sensors as well as other types of sensors, may provide a variety of measurements and/or information. For example, smart clothing can provide information regarding a size of a person's limbs, a smart scale can provide information regarding a person's weight; a smart sphygmomanometer can measure and provide information regarding a person's blood pressure; a smart plate can provide information regarding an amount of food being consumed as well as information regarding an amount of calories and fat content of the food; an altimeter can provide information regarding an altitude of a current location; etc. Many, if not all, of the above-mentioned sensors may wirelessly provide their respective information to a computing device. For example, the information may be provided to a computing device via WiFi, Bluetooth® (Bluetooth is a registered trademark of Bluetooth Sig., Inc., a Delaware Corporation), or other wireless technology. Information may also be provided to the computing device via other methods including, but not limited to, manual entry and a wired connection.

In various embodiments, the computing device may receive and collect data that is provided via the sensors, including the IoT sensors, as well as manually-entered data, and may track the collected data over time. The computing device may analyze the collected data to detect an occurrence of a water retention triggering event (e.g., an event indicating a likely occurrence of an onset of systemic water retention). Water retention triggering events may include, but not be limited to, an increase in weight over a short period of time (for example, 5 pounds in 24 hours), an increase in a size of a limb over a short period of time (for example, a 10% increase in size in 4 hours), a change in blood pressure and an altitude measurement beyond one or more predefined thresholds.

Upon detecting the occurrence of the water retention triggering event, the computing device may determine whether the water retention triggering event is associated with a medical recommendation, which may include a standing order from a doctor or other medical practitioner for reducing an impact of water retention. When the water retention triggering event is associated with a medical recommendation, the medical recommendation may be provided to an individual (e.g., person, patient, caregiver, medical practitioner, etc.) associated with an entity (e.g., person, animal, etc.) experiencing the water retention triggering event. The medical recommendation may be provided via an email, a text message, a voice message or other communication method.

Embodiments of the invention may further proactively anticipate water retention triggering events. For example, some embodiments may analyze a patient's or person's electronic calendar for upcoming events that are likely to cause water retention or that have previously caused water retention. If such an event is found, an associated medical recommendation may be provided to the patient or person.

FIG. 1 illustrates an example environment 100 in which various embodiments may operate. Example environment 100 includes a network 102 to which are connected a computing device 104, a server 106 and databases 108, 110. Computing device 104 may be connected to network 102 via a wireless connection. Although, in some embodiments, computing device 104 may have a wired connection with network 102.

Computing device 104 may include, but not be limited to, a smart phone, a tablet, a laptop personal computer or a desktop personal computer. Server 106 may include, but not be limited to a mainframe computer, a desktop personal computer or a laptop personal computer. Database 108 may include stored therein, for each of a number of entities, information regarding water retention triggering events and any associated medical recommendations. Similarly, database 108 may also include, for each entity, information regarding a number of situations that may pose a water retention risk for individual entities and any associated medical recommendations. Database 110 may include electronic medical records of the entities.

Network 102 may be implemented by any number of any suitable communications media (e.g., wide area network (WAN), local area network (LAN), Internet, Intranet, etc.) or a combination of any of the suitable communications media. Network 102 may include wired and/or wireless networks.

One or more sensors 112 may collect health information of an entity and may provide the health information to at least one computing device such as, for example, computing device 104 or server 106. At least some of the sensors 112 may be Internet of Things (IoT) sensors.

Figure 2:
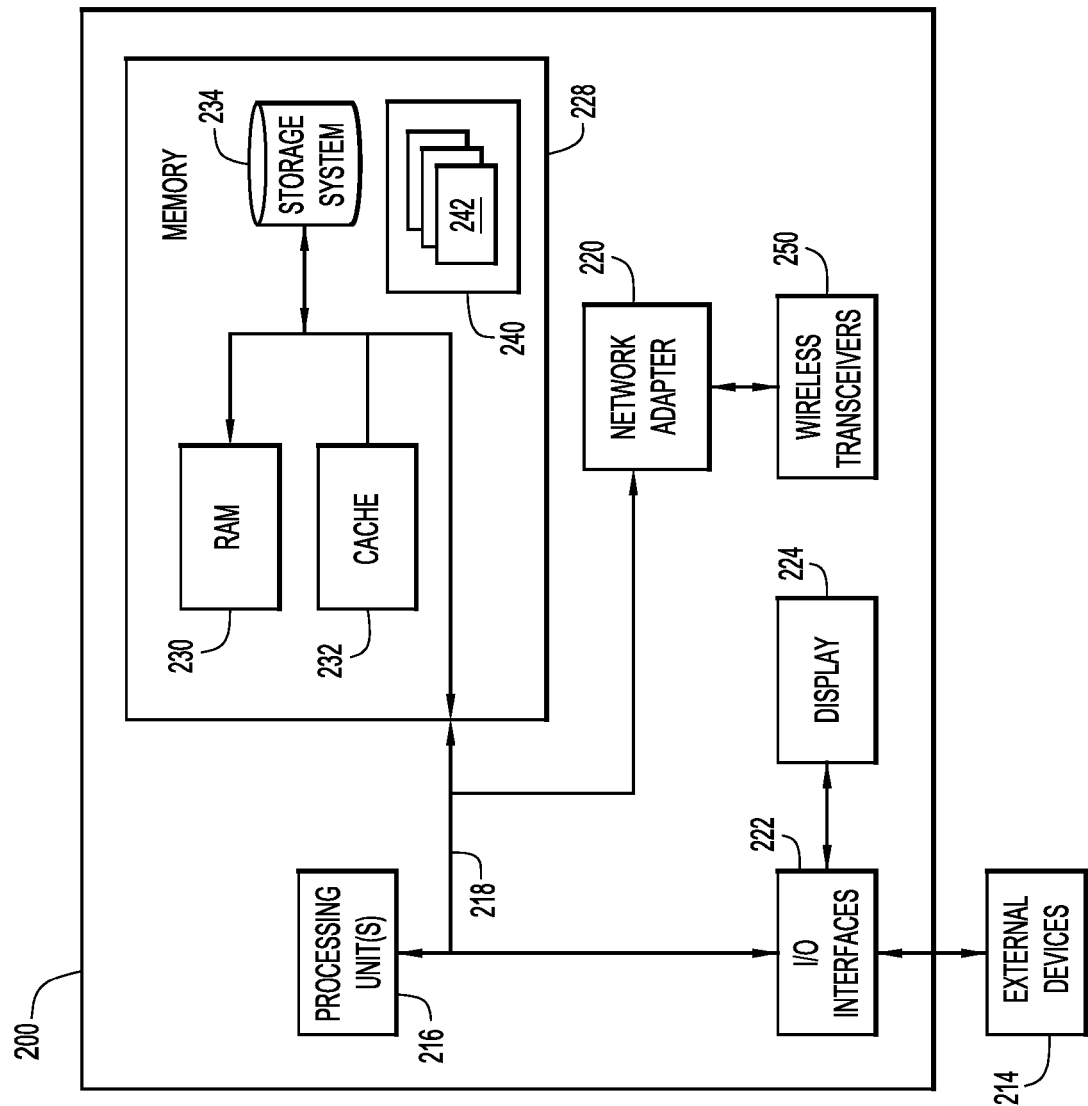
FIG. 2 is a functional block diagram of a computing system that may implement one or more computing devices in various embodiments of the invention.

FIG. 2 is a functional block diagram of a computing system 200 that may implement one or more computing devices such as computing device 104 and/or server 106 in various embodiments of the invention. Computing system 200 is shown in a form of a general-purpose computing device. Components of computing system 200 may include, but are not limited to, one or more processors or processing units 216, a system memory 228, and a bus 218 that couples various system components including system memory 228 to one or more processing units 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computing system 200 typically includes a variety of computer system readable media. Such media may be any available media that is accessible by computing system 200, and may include both volatile and non-volatile media, removable and non-removable media.

System memory 228 can include computer system readable media in the form of volatile memory, such as random access memory (RAM) 230 and/or cache memory 232. Computing system 200 may further include other removable/non-removable, volatile/non-volatile computer system storage media. By way of example only, storage system 234 can be provided for reading from and writing to a non-removable, non-volatile magnetic medium (not shown, which may include a "hard drive" or a Secure Digital (SD) card). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and the program data or some combination thereof, may include an implementation of a networking environment. Program modules 242 generally carry out the functions and/or methodologies of embodiments of the invention as described herein.

Computing system 200 may also communicate with one or more external devices 214 such as a keyboard, a pointing device, one or more displays 224, one or more devices that enable a user to interact with computing system 200, and/or any devices (e.g., network card, modem, etc.) that enable computing system 200 to communicate with one or more other computing devices. Such communication can occur via Input/Output (I/O) interfaces 222. Still yet, computing system 200 can communicate with one or more networks such as a local area network (LAN), a general wide area network (WAN), and/or a public network (e.g., the Internet) via network adapter 220. As depicted, network adapter 220 communicates with the other components of computing system 200 via bus 218. When implementing computing device 104, computing system 200 may further include a wireless transceiver 250 for communicating with sensors 112. The wireless transceiver may communicate via Wi-Fi, Bluetooth® (Bluetooth is a registered trademark of Bluetooth Sig. Inc., incorporated in Delaware) or other wireless communication technology. It should be understood that, although not shown, other hardware and/or software components could be used in conjunction with computing system 200. Examples, include, but are not limited to: microcode, device drivers, redundant processing units, external disk drive arrays, RAID systems, tape drives, and data archival storage systems, etc.

Figure 3:
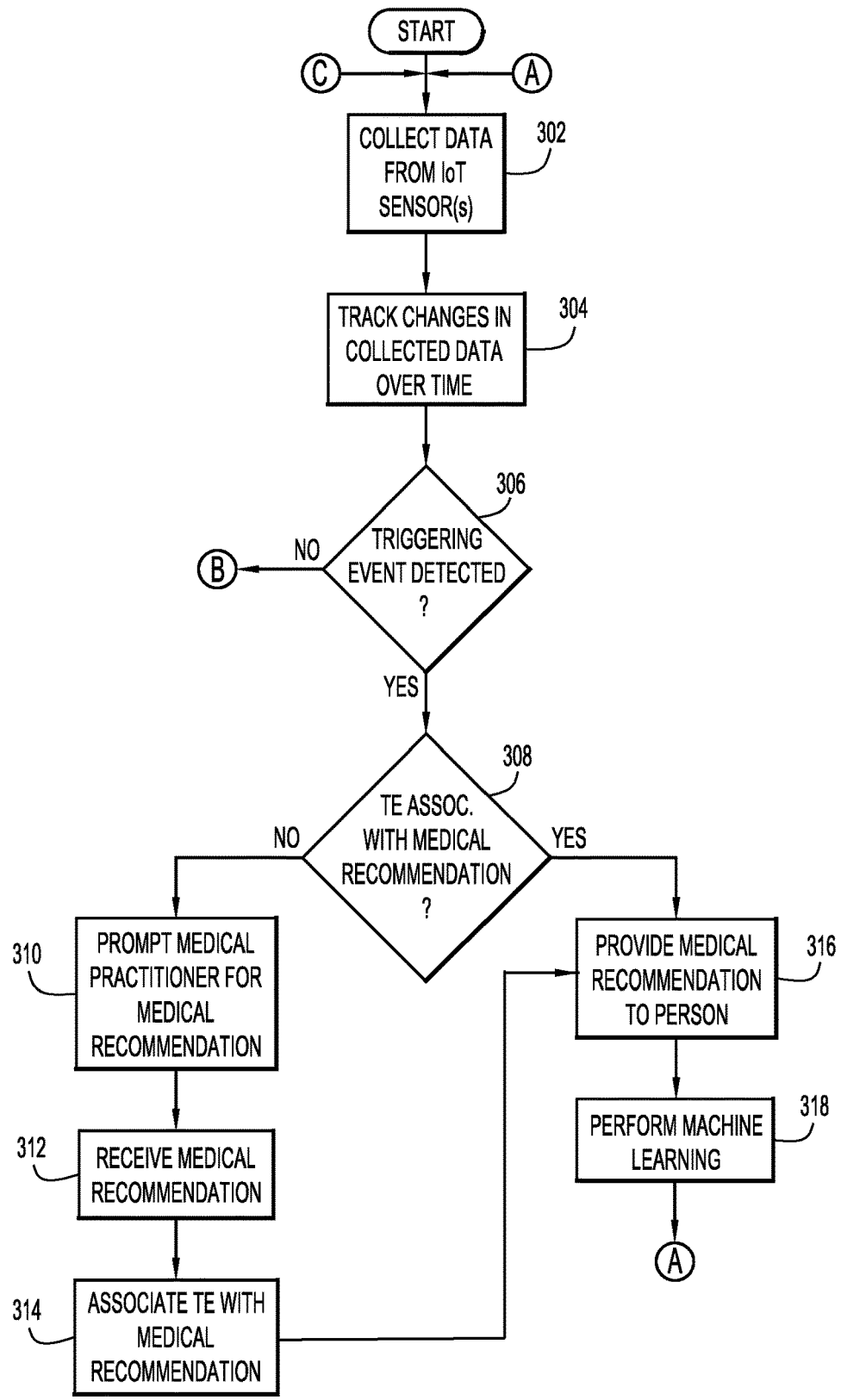
FIGS. 3 and 4 show an example flowchart of a process that may be performed in embodiments of the invention to process monitored data and provide an associated medical recommendation.

FIG. 3 is a flowchart that illustrates an example process that may be performed in various embodiments. The process may begin with computing device 104 collecting data from sensors monitoring an entity, which may include IoT sensors (act 302). In some embodiments, some data may be provided through other approaches, such as, for example, manually provided via computing device 104.

Computing device 104 may provide the collected data to another computing device such as server 106 via network 102. Server 106 may track changes in the collected data over time (act 304). For example, the collected data may include measurement information regarding a limb over a period of time. Tracking changes in the measurement information may reveal a swelling of the limb over a short period of time such as, for example, a few hours.

Server 106 may determine whether a water retention triggering event occurred based on the collected data or the tracked collected data (act 306). In some embodiments, water retention triggering events may be stored in a database such as, for example, remote database 108, which may be accessed by server 106. Server 106 may request data regarding water retention triggering events and associated medical recommendations from a database such as database 108 to determine whether a water retention triggering event occurred. Further, server 106 may download and store the data regarding the water retention triggering events and associated medical recommendations for later use by server 106.

Examples of water retention triggering events may include, but not be limited to: an altimeter reading that is greater than a predefined threshold such as, for example, 8,000 feet above sea level, or another threshold value; an increase in weight of more than a predetermined amount in less than a predetermined time period such as, for example, more than 5 pounds in less than 24 hours; more than a predetermined increase in size of a limb such as, for example, more than a 10% increase in size or a different amount of increase; etc.

If a water retention triggering event is determined to have occurred (act 308), then server 106 may obtain an associated medical recommendation, if one exists, and may provide the medical recommendation to a person or patient, who may be a user of computing device 104 (act 316). The medical recommendation may be provided via any one of a number of methods. For example, the medical recommendation may be sent as an email, as a short message service (SMS) message (also known as a text message), as a voicemail message, or via another method.

Server 106 may then perform machine learning (act 318) in order to learn which types of events may be water retention triggering events. Machine learning is discussed in more detail below. Act 302 may then be performed to collect and process any additional data (act 302).

If, during act 308, the water retention triggering event (TE) is determined to not be associated with a medical recommendation, then server 106 may send a communication with information regarding the water retention triggering event to a doctor or other medical practitioner who may be prompted to provide a medical recommendation (act 310). The medical recommendation provided by the doctor or other medical practitioner may then be received (act 312) and associated with the water retention triggering event (act 314). Acts 316 and 318 may again be performed as previously described.

Figure 4:
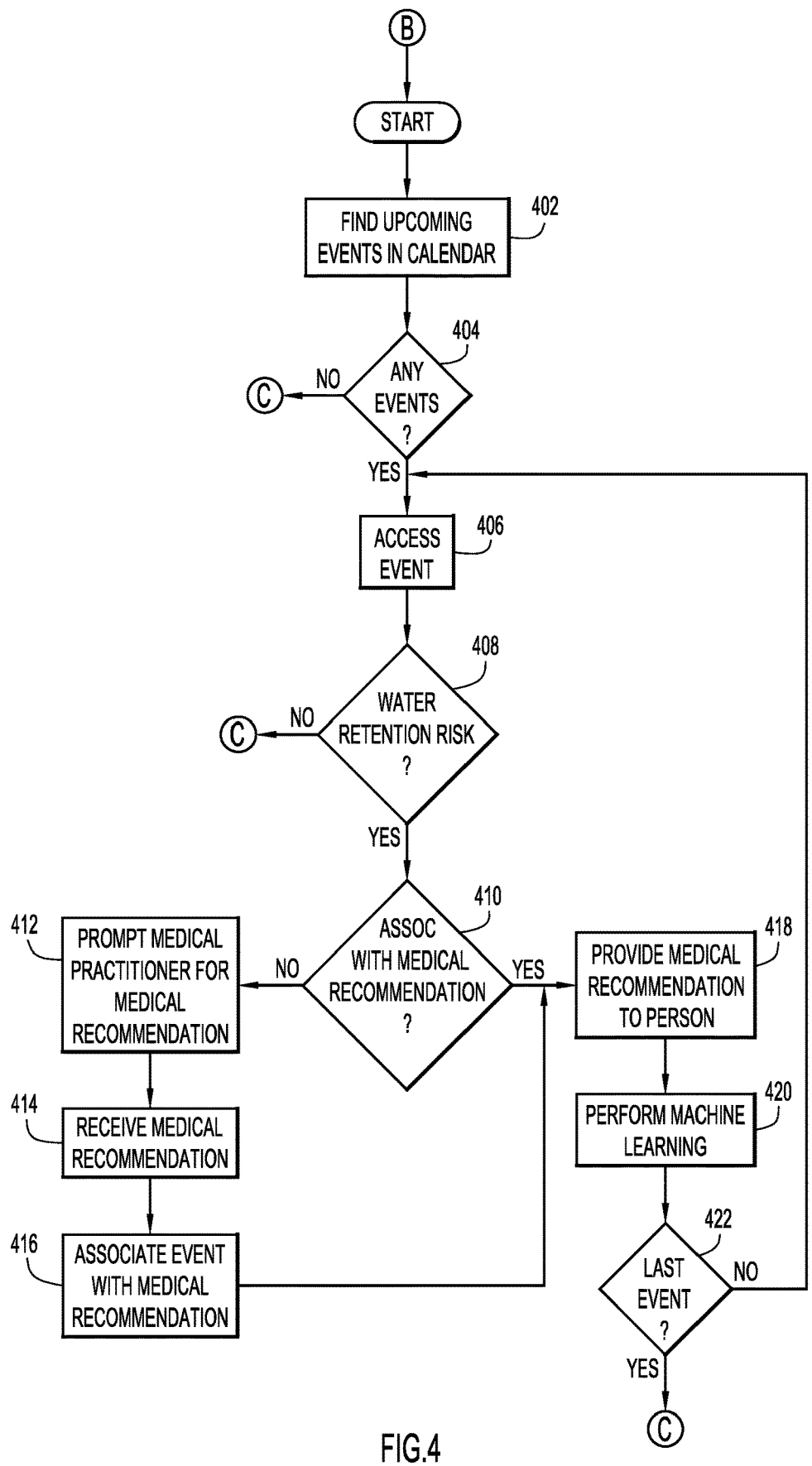

If, during act 306, a water retention triggering event is not detected as having occurred, then server 106 may access an electronic calendar of the person or patient to search for upcoming events (act 402; FIG. 4). An upcoming event is an event that is scheduled to occur within a specific period of time, such as one week, three days, or another period of time. Server 106 may then determine whether any upcoming events are found (act 404). If one or more upcoming events are found, then server 106 may access an event (act 406) and may determine whether the event presents a water retention risk to the person or patient (act 408). Electronic medical records of the person or patient may be accessed in database 110 to make the determination of act 408.

Examples of upcoming events that may present a water retention risk may include, but not be limited to: a scheduled upcoming flight having an expected duration greater than a predetermined amount of time (for example, greater than six hours or another time period); an upcoming event that is a same type of event at which the person or patient previously experienced water retention; an upcoming event at which food that poses a water retention risk may be served, and an upcoming trip to a location having an altitude greater than a predetermined threshold, etc.

If the upcoming event is determined to present a water retention risk, then a determination may be made regarding whether the water retention risk is associated with a medical recommendation (act 410). If the water retention risk is determined to be associated with a medical recommendation, then the medical recommendation may be provided to the patient as previously described (act 418). Machine learning may be performed to improve recognition of types of events that present a water retention risk to the person or patient (act 420). Machine learning is discussed in more detail below. A determination may then be made regarding whether a last upcoming event has been processed (act 422). If the last upcoming event has been processed, then act 302 may be performed again to process the collected data. Otherwise, act 406 may be performed to access a next upcoming event.

If, during act 410, the upcoming event that presents a water retention risk is determined not to be associated with a medical recommendation, then information regarding the upcoming event may be provided to a doctor or other medical practitioner and the doctor or other medical practitioner may be prompted to provide a medical recommendation (act 412). The medical recommendation provided by the doctor or other medical practitioner may be received (act 414) and associated with the upcoming event (act 416). Acts 418-422 may then be performed as previously described.

Act 302 may be performed again to process collected data: if, during act 408, the upcoming event is determined not to be a water retention risk; if, during act 404, no upcoming events are found in the electronic calendar; or if, during act 422, a last upcoming event is determined to have been processed.

In various embodiments, when the collected data is not an exact match to a water retention triggering event, but instead falls somewhere between multiple water retention triggering events, machine learning may be used to determine which of the multiple water retention triggering events best matches the collected data. As recommendations are provided and followed, embodiments may analyze the collected data to determine how an individual's body responds to the recommendations. Embodiments may adjust the recommendations, with approval of a medical practitioner, based on the response to the recommendations by the individual's body.

Based on an individual's electronic calendar, machine learning may learn which activities cause water retention for the individual and a degree of water retention. As an example of two similar activities having different degrees of water retention, going out to eat at a restaurant at which the individual orders a salty soup is different than going out to a different restaurant and ordering a salad.

Further, events are not necessarily isolated. Continuing with the salty soup example, the individual may have an activity such as, for example, exercise scheduled on his or her electronic calendar. The exercise will help to move fluid out of the individual's legs, thereby reducing the water retention risk. On the other hand, the individual may be scheduled to go on a flight, which may increase the water retention risk. An impact of combinations and permutations of activities may affect a risk-reward scenario and the various embodiments may determine an impact of the combined events. As all of the activities are combined, an impact on a risk of a water retention occurrence may increase or decrease. Thus, an effect of the combined activities may produce a current risk score and a recommendation may be affected by the current risk score (e.g., take medication vs. drink more water).

Machine learning training may occur over time. Collected data may be mostly individual-based. However, the data could be crowd-sourced such that machine learning can learn, for example, that an impact of using a treadmill, with respect to water retention risk, is similar to an impact of using a stepper, but is different from an impact of using a ski machine.

If an upcoming event on the electronic calendar had not previously been scheduled, then crowd-sourced data may be used, at least initially, and an assumption is made that the individual's water retention risk regarding the upcoming event is similar to the water retention risk of others, with a similar profile history, who previously had a similar scheduled upcoming event on their electronic calendars. Due to machine learning, embodiments become more useful over a period of time as a history of data is created and maintained.

Figure 5:
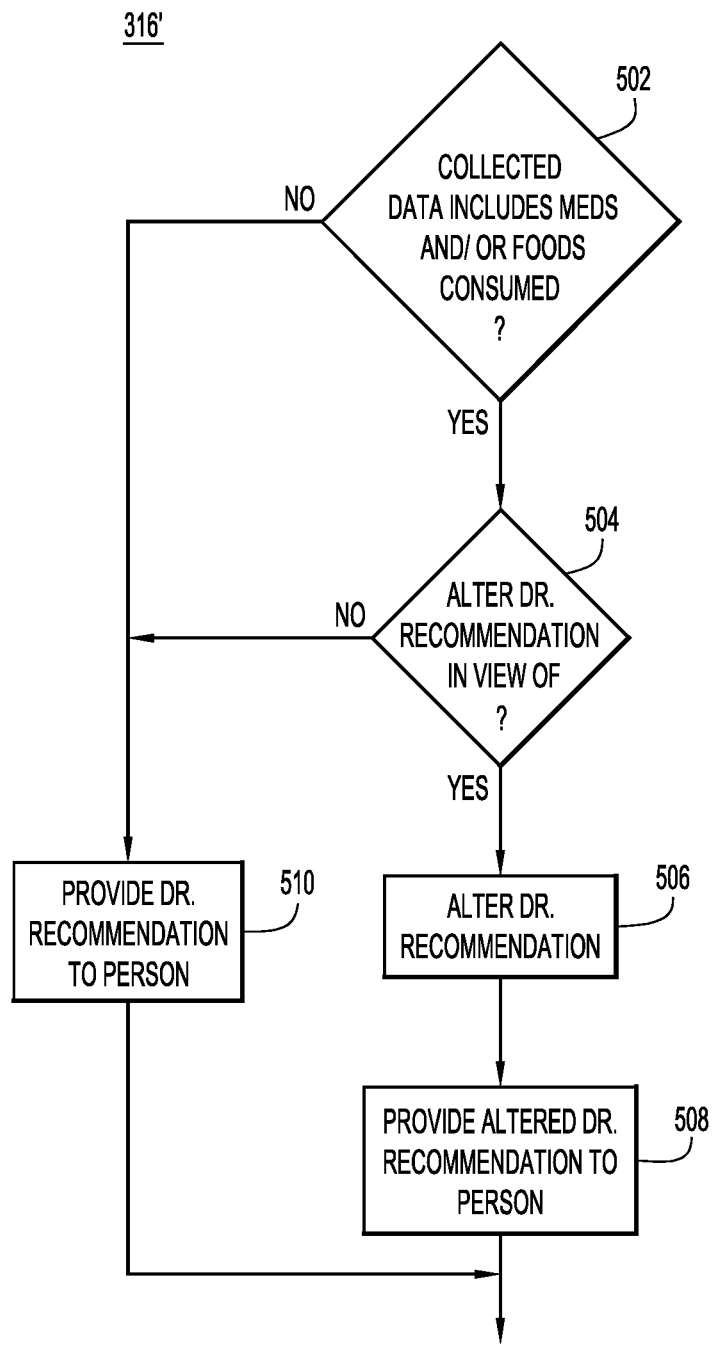
FIG. 5 is a flowchart of a variation of the process shown in FIG. 3 in which a medical recommendation may be altered or replaced after considering whether medicine was taken or food was consumed.

In a variation of some embodiments, before providing a medical recommendation to the patient, any food consumed or medications taken may be considered and may result in an altered, or different, medical recommendation. In the variation, act 316 from FIG. 3 may be replaced with 316' of FIG. 5. According to the variation, if the collected data is determined to include information regarding any medications taken and/or foods consumed (act 502; FIG. 5), then a determination may be made regarding whether the provided medical recommendation is to be altered or replaced with a different medical recommendation, which was provided by the doctor or other medical practitioner and which considers the medications taken and/or the foods consumed (act 504). If the provided medical recommendation is to be altered or replaced, then the medical recommendation is altered or replaced, taking into consideration the medications taken and/or the food consumed (act 506) and the altered or replaced medical recommendation may then be provided to the patient as previously described (act 508).

If, during act 502, the collected data is determined not to include information regarding medications taken and/or foods consumed, or if, during act 504, a determination is made that the medical recommendation is not to be altered, then the medical recommendation may be provided to the patient as previously described (act 510).

Just as a combination of events or activities can affect a water retention risk, which machine learning can learn, the water retention risk can be affected by a number of different combinations. For example, the water retention risk may be affected by any combination of food, activity, humidity, temperature, degree of response, medications taken, etc. Machine learning can learn the individual's body response to the combinations and can provide more insight to a medical practitioner with regard to adjusting the recommendations for the individual or adjusting a threshold for the water retention events for the individual.

The above acts may be performed by computing device 104 and/or server 106 in any desired fashion.

It will be appreciated that the embodiments described above and illustrated in the drawings represent only a few of the many ways of implementing various embodiments.

The environment of the present invention embodiments may include any number of computer or other processing systems and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various computing systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures to store information. The database system may be included within or coupled to server and/or client systems. The database systems and/or storage structures may be remote from or local to a computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the FIGS. illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figs. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for monitoring an entity for personalized water retention management comprising:
   collecting, by at least one computing device, health data for the entity generated and electronically received from one or more sensors monitoring a body of the entity for any change indicating an occurrence of an onset of water retention, changes indicating the occurrence of the onset of the water retention including a weight change exceeding a predefined weight limit within a first predefined period of time, and an increase in a size of a limb exceeding a predefined size increase within a second predefined period of time;
   tracking, by the at least one computing device, changes over time in the collected health data;
   detecting, by the at least one computing device, the occurrence of the onset of the water retention based on the collected health data including at least one of the changes, the occurrence of the onset of the water retention being associated with a medical recommendation;
   electronically providing, by the at least one computing device, the medical recommendation to the entity responsive to the detecting of the occurrence of the onset of the water retention;
   finding, by the at least one computing device, a plurality of upcoming scheduled activities occurring at most three days apart in an electronic calendar of the entity;
   responsive to determining, by the at least one computing device, that an upcoming scheduled activity is a new activity that had not been previously scheduled in the electronic calendar:
      predicting, by the at least one computing device, whether the scheduled activity will cause the occurrence of the onset of the water retention for the entity based on machine learning techniques trained over time and applied to crowd-sourced data including water retention risk data of others assumed to have a water retention risk similar to a water retention risk of the entity and who previously had a similar scheduled activity on their respective electronic calendars;
   responsive to determining, by the at least one computing device, that the plurality of upcoming scheduled activities have been previously scheduled in the electronic calendar of the entity:
      determining, by the at least one computing device, an impact of each of the plurality of upcoming scheduled activities to a risk of water retention, wherein at least one upcoming scheduled activity decreases the risk of water retention and at least one upcoming scheduled activity increases the risk of water retention, and wherein the plurality of upcoming scheduled activities includes an exercise activity and consumption of food;
      combining, by the at least one computing device using machine learning techniques trained over time, the impact of each of the plurality of upcoming scheduled activities to determine a risk score indicating the risk of water retention; and
      determining, by the at least one computing device, based on the risk score, whether the upcoming scheduled activities will cause the entity to experience the water retention;
   storing in a database, by the at least one computing device, information regarding one or more of the found upcoming scheduled activities that cause the entity to experience the water retention; and
   electronically providing, by the at least one computing device, a second medical recommendation to the entity based on the found upcoming scheduled activities when the found upcoming scheduled activities are expected to cause an occurrence of the water retention for the entity.

2. The computer-implemented method of claim 1, further comprising:
   determining, by the at least one computing device, a second occurrence of the onset of the water retention not associated with any medical recommendation based on the collected health data;
   prompting, by the at least one computing device, a medical practitioner for a new medical recommendation responsive to the determining the second occurrence of the onset of the water retention not associated with the any medical recommendation;
   receiving, by the at least one computing device, the new medical recommendation in response to the prompting;

associating, by the at least one computing device, the received new medical recommendation with the second occurrence of the onset of the water retention; and providing the new medical recommendation to the entity.

3. The computer-implemented method of claim 1, further comprising:

presenting information to a medical practitioner regarding the found upcoming scheduled activities when the found upcoming scheduled activities are predicted to cause the occurrence of the onset of the water retention not associated with any medical recommendation, the presenting further comprising:
 requesting the medical practitioner to provide a medical recommendation regarding the found upcoming scheduled activities, and
 upon receiving the requested medical recommendation, providing the requested medical recommendation to the entity.

4. The computer-implemented method of claim 3, further comprising:

associating the received requested medical recommendation with the found upcoming scheduled activities when the requested medical recommendation is received.

5. The computer-implemented method of claim 1, wherein:

the monitored health data includes information regarding an altitude of the entity; and the computer-implemented method further comprises:
 determining an altitude-related medical recommendation associated with the altitude; and
 providing the altitude-related medical recommendation to the entity.

6. The computer-implemented method of claim 1, further comprising:

receiving information regarding at least one of foods consumed and medications taken by the entity, wherein the detecting the occurrence of the onset of the water retention associated with the provided medical recommendation is further based on the at least one of the foods consumed and the medications taken.

7. A system for monitoring an entity for personalized water retention management comprising:

at least one processor; and at least one memory connected with each of the at least one processor, wherein the at least one processor is configured to perform:
 collecting health data for the entity generated and electronically received from one or more sensors monitoring a body of the entity for any change indicating an occurrence of an onset of water retention, changes indicating the occurrence of the onset of the water retention including a weight change exceeding a predefined weight limit within a first predefined period of time, and an increase in a size of a limb exceeding a predefined size increase within a second predefined period of time;
 tracking changes over time in the collected health data;
 detecting the occurrence of the onset of the water retention based on the collected health data including at least one of the changes, the occurrence of the onset of the water retention being associated with a medical recommendation;
 electronically providing the medical recommendation to the entity responsive to the detecting of the occurrence of the onset of the water retention;
 finding a plurality of upcoming scheduled activities occurring at most three days apart in an electronic calendar of the entity;
 responsive to determining that an upcoming scheduled activity is a new activity that had not been previously scheduled in the electronic calendar:
  predicting whether the scheduled activity will cause the occurrence of the onset of the water retention for the entity based on machine learning techniques trained over time and applied to crowd-sourced data including water retention risk data of others assumed to have a water retention risk similar to a water retention risk of the entity and who previously had a similar scheduled activity on their respective electronic calendars;
 responsive to determining that the plurality of upcoming scheduled activities have been previously scheduled in the electronic calendar of the entity:
  determining an impact of each of the plurality of upcoming scheduled activities to a risk of water retention, wherein at least one upcoming scheduled activity decreases the risk of water retention and at least one upcoming scheduled activity increases the risk of water retention, and wherein the plurality of upcoming scheduled activities includes an exercise activity and consumption of food;
  combining, using machine learning techniques trained over time, the impact of each of the plurality of upcoming scheduled activities to determine a risk score indicating the risk of water retention; and
  determining, based on the risk score, whether the upcoming scheduled activities will cause the entity to experience the water retention;
 storing in a database information regarding one or more of the found upcoming scheduled activities that cause the entity to experience the water retention; and
 electronically providing a second medical recommendation to the entity based on the found upcoming scheduled activities when the found upcoming scheduled activities are expected to cause an occurrence of the water retention for the entity.

8. The system of claim 7, wherein the at least one processor is further configured to perform:

determining a second occurrence of the onset of the water retention not associated with any medical recommendation based on the collected health data;

prompting a medical practitioner for a new medical recommendation responsive to the determining the second occurrence of the onset of the water retention not associated with the any medical recommendation;

receiving the new medical recommendation in response to the prompting;

associating the received new medical recommendation with the second occurrence of the onset of the water retention; and providing the new medical recommendation to the entity.

9. The system of claim 7, wherein the at least one processor is further configured to perform:

presenting information to a medical practitioner regarding the found upcoming scheduled activities when the found upcoming scheduled activities are predicted to cause the occurrence of the onset of the water retention not associated with any medical recommendation, the presenting further comprising:

requesting the medical practitioner to provide a medical recommendation regarding the found upcoming scheduled activities, and upon receiving the requested medical recommendation, providing the requested medical recommendation to the entity.

10. The system of claim 9, wherein the at least one processor is further configured to perform:

associating the received requested medical recommendation with the found upcoming scheduled activities when the requested medical recommendation is received.

11. The system of claim 7, wherein:

the monitored health data includes information regarding an altitude of the entity; and the at least one processor is further configured to perform:

determining an altitude-related medical recommendation associated with the altitude; and providing the altitude-related medical recommendation to the entity.

12. The system of claim 7, wherein the at least one processor is further configured to perform:

receiving information regarding at least one of foods consumed and medications taken by the entity, wherein the detecting the occurrence of the onset of the water retention associated with the provided medical recommendation is further based on the at least one of the foods consumed and the medications taken.

13. A computer program product comprising at least one computer readable storage medium having computer readable program code embodied therewith for execution on at least one processor, the computer readable program code being configured to be executed by the at least one processor to perform:

collecting health data for an entity generated and electronically received from one or more sensors monitoring a body of the entity for any change indicating an occurrence of an onset of water retention, changes indicating the occurrence of the onset of the water retention including a weight change exceeding a predefined weight limit within a first predefined period of time, and an increase in a size of a limb exceeding a predefined size increase within a second predefined period of time;

tracking changes over time in the collected health data;

detecting the occurrence of the onset of the water retention based on the collected health data including at least one of the changes, the occurrence of the onset of the water retention being associated with a medical recommendation;

electronically providing the medical recommendation to the entity responsive to the detecting of the occurrence of the onset of the water retention;

finding a plurality of upcoming scheduled activities occurring at most three days apart in an electronic calendar of the entity;

responsive to determining that an upcoming scheduled activity is a new activity that had not been previously scheduled in the electronic calendar:

predicting whether the scheduled activity will cause the occurrence of the onset of the water retention for the entity based on machine learning techniques trained over time and applied to crowd-sourced data including water retention risk data of others assumed to have a water retention risk similar to a water retention risk of the entity and who previously had a similar scheduled activity on their respective electronic calendars;

responsive to determining that the plurality of upcoming scheduled activities have been previously scheduled in the electronic calendar of the entity:

determining an impact of each of the plurality of upcoming scheduled activities to a risk of water retention, wherein at least one upcoming scheduled activity decreases the risk of water retention and at least one upcoming scheduled activity increases the risk of water retention, and wherein the plurality of upcoming scheduled activities includes an exercise activity and consumption of food;

combining, using machine learning techniques trained over time, the impact of each of the plurality of upcoming scheduled activities to determine a risk score indicating the risk of water retention; and determining, based on the risk score, whether the upcoming scheduled activities will cause the entity to experience the water retention;

storing in a database information regarding one or more of the found upcoming scheduled activities that cause the entity to experience the water retention; and electronically providing a second medical recommendation to the entity based on the found upcoming scheduled activities when the found upcoming scheduled activities are expected to cause an occurrence of the water retention for the entity.

14. The computer program product of claim 13, wherein the computer readable program code is further configured to be executed by the at least one processor to perform:

determining a second occurrence of the onset of the water retention not associated with any medical recommendation based on the collected health data;

prompting a medical practitioner for a new medical recommendation responsive to the determining the second occurrence of the onset of the water retention not associated with the any medical recommendation;

receiving the new medical recommendation in response to the prompting;

associating the received new medical recommendation with the second occurrence of the onset of the water retention; and providing the new medical recommendation to the entity.

15. The computer program product of claim 13, wherein the computer readable program code is further configured to be executed by the at least one processor to perform:

presenting information to a medical practitioner regarding the found upcoming scheduled activities when the found upcoming scheduled activities are predicted to cause the occurrence of the onset of the water retention not associated with any medical recommendation, the presenting further comprising:

requesting the medical practitioner to provide a medical recommendation regarding the found upcoming scheduled activities, and upon receiving the requested medical recommendation, providing the requested medical recommendation to the entity.

16. The computer program product of claim 13, wherein:

the monitored health data includes information regarding an altitude of the entity; and the computer readable program code is further configured to be executed by the at least one processor to perform:

determining an altitude-related medical recommendation associated with the altitude; and providing the altitude-related medical recommendation to the entity.

17. The computer program product of claim 13, wherein the computer readable program code is further configured to be executed by the at least one processor to perform:
receiving information regarding at least one of foods consumed and medications taken by the entity, wherein the determining the occurrence of the onset of the water retention associated with the provided medical recommendation is further based on the at least one of the foods consumed and the medications taken.

* * * * *